(12) United States Patent
Vodyanoy et al.

(10) Patent No.: US 7,022,514 B2
(45) Date of Patent: Apr. 4, 2006

(54) USE OF ACACIA GUM TO ISOLATE AND PRESERVE BIOLOGICAL MATERIAL

(75) Inventors: Vitaly J. Vodyanoy, Auburn, AL (US); James M. Barbaree, Dadeville, AL (US); Bryan A. Chin, Auburn, AL (US); William Charles Neely, Auburn, AL (US); Suram T. Pathirana, Sunnyvale, CA (US); Timothy D. Braden, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 10/000,727

(22) Filed: Nov. 30, 2001

(65) Prior Publication Data

US 2003/0138939 A1 Jul. 24, 2003

Related U.S. Application Data

(60) Provisional application No. 60/250,798, filed on Dec. 1, 2000, and provisional application No. 60/250,799, filed on Dec. 1, 2000.

(51) Int. Cl.
- *C12N 1/04* (2006.01)
- *C12N 5/06* (2006.01)
- *C12Q 1/68* (2006.01)
- *A01N 63/02* (2006.01)
- *A61K 35/78* (2006.01)

(52) U.S. Cl. ........................... 435/260; 424/725

(58) Field of Classification Search ............ 435/6, 435/260, 324, 374, 806, 822, 849; 424/93.1, 424/93.4, 93.48, 725
See application file for complete search history.

(56) References Cited

U.S. PATENT DOCUMENTS

| | | |
|---|---|---|
| 3,235,337 A | 2/1966 | Artis |
| 3,645,852 A | 2/1972 | Axén et al. |
| 4,021,368 A | 5/1977 | Nemec et al. |
| 4,115,534 A | 9/1978 | Ithakissios |
| 4,284,553 A | 8/1981 | Brown et al. |
| 4,329,337 A | 5/1982 | Sexton |
| 4,391,909 A * | 7/1983 | Lim ......................... 435/1.1 |
| 4,416,813 A | 11/1983 | Ikeda et al. |
| 4,504,582 A | 3/1985 | Swann |
| 4,588,584 A | 5/1986 | Lumsden et al. |
| 4,610,962 A | 9/1986 | Takagi et al. |
| 4,632,904 A | 12/1986 | Lee |
| 4,659,664 A | 4/1987 | de Buda |
| 4,673,566 A | 6/1987 | Goosen et al. |
| 4,708,932 A | 11/1987 | Axén et al. |
| 4,933,284 A | 6/1990 | Lapins et al. |
| 4,959,305 A | 9/1990 | Woodrum |
| 4,971,783 A | 11/1990 | Bolton et al. |
| 4,975,224 A | 12/1990 | Pringle |
| 5,034,428 A | 7/1991 | Hoffman et al. |
| 5,096,481 A | 3/1992 | Sylvia et al. |
| 5,116,747 A | 5/1992 | Moo-Young et al. |
| 5,144,008 A | 9/1992 | Ikeda et al. |
| 5,227,298 A | 7/1993 | Weber et al. |
| 5,268,286 A | 12/1993 | Kobayashi et al. |
| 5,318,382 A | 6/1994 | Cahill |
| 5,427,935 A | 6/1995 | Wang et al. |
| 5,474,890 A | 12/1995 | Di Virgilio et al. |
| 5,550,178 A | 8/1996 | Desai et al. |
| 5,554,386 A | 9/1996 | Groman et al. |
| 5,627,063 A | 5/1997 | Divies et al. |
| 5,707,443 A | 1/1998 | Brown et al. |
| 5,714,340 A | 2/1998 | Sutton et al. |
| 5,728,350 A | 3/1998 | Kinoshita et al. |
| 5,770,370 A | 6/1998 | Kumar |
| 5,795,570 A | 8/1998 | Weber et al. |
| 5,827,707 A | 10/1998 | Lamberti |

(Continued)

FOREIGN PATENT DOCUMENTS

| | | |
|---|---|---|
| DE | 3733551 A1 | 4/1989 |
| DE | 3733551 C2 | 4/1989 |
| EP | 0 699 905 A | 3/1996 |
| GB | 865239 A | 4/1961 |
| GB | 2 093 040 A | 8/1982 |

OTHER PUBLICATIONS

Yokohama, et al., "Deep Freezing of Horse Erythrocytes Cryo–protective Agents and Properties of the Cells Frozen Stored for 4 Years," Japanese Journal of Zootechnical Science; 1981; Abstract; pp. 487–492, vol. 52, No. 7.

Munderloh, et al., "Isolation of the Equine Granulocytic Ehrlichiosis Agent, *Ehrlichia Equi*, in Tick Cell Culture," Journal of Clinical Microbiology; 1996; Abstract; pp. 664–670, vol. 34, No. 3.

International Searching Authority; International Search Report and Written Opinion; mailed Nov. 24, 2004; regarding International Application No. PCT/US2004/017872, "Use of Gum Acacia to Contain and Preserve a Biohazard" (European Patent Office).

International Searching Authority; International Search Report and Written Opinion; mailed Nov. 25, 2004; regarding International Application No. PCT/US2004/017873, "Use of Gum Acacia to Contain a Radiological Hazard" (European Patent Office).

*Primary Examiner*—Ralph Gitomer
*Assistant Examiner*—Kailash C. Srivastava
(74) *Attorney, Agent, or Firm*—Andrus, Sceales, Starke & Sawall

(57) ABSTRACT

Compositions and methods for the reversible preservation of biological samples are provided. The compositions include *Acacia* Gum, including derivations and modifications thereof which are useful as a reversible preservation solution. A method is provided for using *Acacia* Gum to isolate and reversibly preserve a biological specimen in a dormant state at room temperature for an extended period with minimal damage to the specimen. The compositions and methods disclosed may also be used to create reversibly preserved biological specimens and biological receptors for use in biosensors.

16 Claims, 4 Drawing Sheets

U.S. PATENT DOCUMENTS

| | | |
|---|---|---|
| 5,849,274 A | 12/1998 | Gers-Barlag et al. |
| 5,866,356 A | 2/1999 | Albert et al. |
| 5,916,029 A | 6/1999 | Smith et al. |
| 6,043,067 A | 3/2000 | Lihme et al. |
| 6,130,034 A | 10/2000 | Aitken |
| 6,140,121 A | 10/2000 | Ellington et al. |
| 6,309,815 B1 | 10/2001 | Tash et al. |
| 6,391,296 B1 | 5/2002 | Okano et al. |
| 6,413,713 B1 | 7/2002 | Serebrennikov |
| 6,420,171 B1 | 7/2002 | Nakamura et al. |
| 6,472,160 B1 | 10/2002 | Saruta et al. |
| 6,593,309 B1 | 7/2003 | Ellington et al. |
| 6,596,310 B1 | 7/2003 | Chou et al. |
| 6,649,384 B1 | 11/2003 | Walsh et al. |
| 6,828,090 B1 | 12/2004 | Lucas et al. |
| 2003/0091971 A1 | 5/2003 | Xia et al. |
| 2003/0100103 A1 | 5/2003 | Saruta et al. |
| 2003/0104506 A1 | 6/2003 | Durst et al. |

* cited by examiner

USE OF ACACIA GUM TO ISOLATE AND PRESERVE BIOLOGICAL MATERIAL

RELATED APPLICATIONS

This application claims the benefit and priority of pending U.S. Provisional Application having Ser. No. 60/250,798, filed on Dec. 1, 2000, entitled "Method of Protection of Biosensor Surface," and pending U.S. Provisional Application having Ser. No. 60/250,799, also filed on Dec. 1, 2000, entitled "Method for Protection of Biological Material," both of which are incorporated herein by reference.

TECHNICAL FIELD

The present invention relates generally to the field of biological sample preservation and, more particularly, to a method of using a solution of *Acacia* Gum to preserve a biological specimen in a dormant state and, later, using an aqueous solution to restore the specimen unharmed to its isolated condition.

BACKGROUND OF THE INVENTION

Various methods for the preservation of biological specimens have evolved over the years. Modem specimen preparation techniques for microbiology and electron microscopy typically include dehydration and immobilization, both of which are irreversible and often damage the integrity of the specimen.

Dehydration using chemicals or freezing temperatures typically causes structural damage to biological tissues. Chemicals may destroy the overall quality of the specimen, including the particular characteristics of interest to the scientist. Rapid freeze-drying often produces crystalline structures that are destructive to most biological tissues. The result of dehydration is a biological sample that has been significantly altered, beyond repair, from its natural state.

Immobilization of a biological sample within a polymer typically involves curing, using elevated temperatures or ultraviolet radiation, both of which are detrimental to specimen quality. The polymers and resins typically used for sample preparation today form a hard plastic when cured. Once a sample has been cured, the biological material cannot be restored to its isolated state.

Biological specimen preservation techniques are of particular concern in the preparation of biosensors. Biosensors are used in the health and environmental sciences for rapid detection of specific substances. Biosensors are currently used to detect the presence of pesticides, herbicides, and other compounds; to detect the presence of organic compounds such as alcohols, ammonia, and metals; and, to detect the presence of specific bacteria including algae, fungi, and pathogenic organisms such as *Escherichia coli* (*E. coli*) and *Salmonella*. Potential applications for biosensors include sensing pollution and microbial contamination of air and water, clinical diagnosis of medical conditions, fermentation analysis and control, monitoring and analysis of industrial gases and liquids, monitoring of mining conditions and sensing toxic gases.

Biosensors often have a very short shelf life because the antibody or other biological receptor degrades rapidly when exposed to the environment. Like other biological samples, biological receptors need isolation and protection from the environment until ready for use. In field applications, especially, a variety of biological receptors may be needed at any time, depending upon the conditions.

There is an unsatisfied need in the art for biological samples that can be protected and preserved without altering or destroying the biological tissue. The demand for safe transport and prolonged storage of biological samples today requires preservation techniques that maintain the integrity and quality of the biological sample. Sensitive biological receptors used in biosensors need to be isolated from the environment, without damaging the receptor, until ready for use. None of the specimen preparation techniques in the art currently meet these needs.

There is also a need in the art for biological samples that can be restored to their isolated or prepared state after immobilization, with minimal damage, for later study or use. The current techniques of dehydration and immobilization are irreversible and destroy sample viability. Restoration is particularly critical for the biological receptors in biosensors, which are especially sensitive. There is a need, therefore, for a preservation technique that is both harmless and reversible.

SUMMARY OF THE INVENTION

The above and other needs are met by the present invention which, stated generally, provides a method of using *Acacia* Gum to isolate and preserve biological material without damage to the specimen. The present invention further provides reversible techniques for using *Acacia* Gum that maintain the integrity and viability of biological specimens, even after prolonged storage at room temperature.

In one aspect of the invention, a reversibly preserved biological specimen is provided. The specimen in an isolated condition has been combined with an effective amount of a solution of solid *Acacia* Gum dissolved in water. The suspension has been cured in ambient conditions to form a solid that can later be restored to a suspension. In one aspect, the suspension is capable of being separated so that the biological specimen can be restored to its former, isolated condition. In one embodiment, the biological specimen may include a separate container holding an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the invention, a method of reversibly preserving a biological specimen includes the steps of combining the specimen in an isolated condition with an effective amount of an *Acacia* Gum solution to form a suspension and, then, curing the suspension in ambient conditions to form a solid. The preservation method may also include the steps of irrigating the solid in ambient conditions with an effective amount of an aqueous solution to restore the suspension and then separating the solution from the specimen to restore the specimen to its former, isolated condition.

In one embodiment, the *Acacia* Gum solution is formed by dissolving solid *Acacia* Gum in distilled water. The combining step may include immersing the specimen in the *Acacia* Gum solution. The curing step may include stirring the suspension.

In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

The biological specimens suitable for preservation may be microorganisms, viruses, bacteria, phages, antibodies, antigens, DNA, RNA, receptors, enzymes, proteins, biochemicals, yeast, fungi, plant and animal cells and extracts, semen, sperm, ova, blood, tissue samples, cell samples, urine, saliva, lymphatic fluid, skin, hair, bones, or bone marrow. In one embodiment, the biological specimen may be a biosensor.

In another aspect of the invention, a method of fabricating a reversibly preserved biological specimen includes the steps of combining the biological specimen in an isolated condition with an effective amount of an *Acacia* Gum solution to form a suspension and, then, curing the suspension in ambient conditions to form a solid that can later be restored to a suspension. In one aspect, the suspension is capable of being separated so that the biological specimen can be restored to its former, isolated condition.

In one embodiment, the *Acacia* Gum solution used in this method of fabrication is formed by dissolving solid *Acacia* Gum in distilled water. The curing step may include stirring the suspension. The combining step may include immersing the specimen.

In one embodiment, the method may include providing an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the invention, a method of restoring the biological receptor includes the steps of irrigating the solid in ambient conditions with an effective amount of an aqueous solution to restore the suspension and, then, separating the solution from the biological receptor such that the biological receptor is substantially restored to its former, isolated condition. In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

In another aspect of the invention, a biosensor having a reversibly preserved biological receptor includes a signal transducer, an interface connected to the signal transducer, and a solid containing the biological receptor. The solid has been formed by curing a suspension in ambient conditions. The suspension includes the biological receptor in its prepared condition and an effective amount of an *Acacia* Gum solution. The suspension is capable of being separated so that the biological receptor can be restored to its former, prepared condition.

In one embodiment, the *Acacia* Gum solution is formed by dissolving solid *Acacia* Gum in distilled water. The biological receptors suitable for preservation may be microorganisms, viruses, bacteria, phages, antibodies, antigens, DNA, RNA, receptors, enzymes, proteins, biochemicals, yeast, fungi, plant and animal cells and extracts, semen, sperm, ova, blood, tissue samples, cell samples, urine, saliva, lymphatic fluid, skin, hair, bones, or bone marrow.

In one embodiment, the biosensor may include a separate container holding an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the present invention, a method of reversibly preserving a biological receptor includes the steps of combining the receptor in its prepared condition with an effective amount of an *Acacia* Gum solution to form a suspension and, then, curing the suspension in ambient conditions to form a solid. The preservation method may also include the steps of irrigating the solid in ambient conditions with an effective amount of an aqueous solution to restore the suspension and then separating the solution from the receptor to restore the receptor to its former, prepared condition.

In one embodiment, the *Acacia* Gum solution is formed by dissolving solid *Acacia* Gum in distilled water. The curing step may include stirring the suspension.

In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

In another aspect of the invention, a method of fabricating a reversibly preserved biological receptor disposed upon the interface of a biosensor includes the steps of combining the biological receptor in its prepared condition with an effective amount of an *Acacia* Gum solution to form a suspension and, then, curing the suspension in ambient conditions to form a solid that can later be restored to a suspension. In one aspect, the suspension is capable of being separated so that the biological receptor can be restored to its former, prepared condition.

In one embodiment, the *Acacia* Gum solution used in this method of fabrication is formed by dissolving solid *Acacia* Gum in distilled water. The curing step may include stirring the suspension. The combining step may include immersing the receptor.

In one embodiment, the method may include providing an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the invention, a method of restoring the biological receptor includes the steps of irrigating the solid in ambient conditions with an effective amount of an aqueous solution to restore the suspension and, then, separating the solution from the biological receptor such that the biological receptor is substantially restored to its former, prepared condition. In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

In another aspect of the invention, a water-soluble solid for reversibly preserving a biological specimen includes a suspension formed by combining the biological specimen in an isolated condition and an effective amount of a solution of solid *Acacia* Gum dissolved in water and an effective amount of aqueous solution to restore the suspension by irrigating the solid in ambient conditions with the aqueous solution.

In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

Thus, it is an object of the present invention to provide compositions and methods for protecting and preserving biological samples without altering or destroying the biological tissue. It is a related object to provide preservation techniques that maintain the integrity and quality of the biological sample.

It is a further object of the present invention to provide biological samples that can be restored to their isolated or prepared state after immobilization, with minimal damage, for later study or use. It is a related object of the present invention to provide a preservation technique that is both harmless and reversible.

It is a further object of the present invention to provide methods for restoring biological specimens and receptors to their former conditions without a significant loss in viability or function.

It is another object of the present invention to provide biosensors with biological receptors that can be restored to their prepared state after immobilization, with minimal damage, for later study or use.

It is yet another object of the present invention to provide a water-soluble solid for preserving biological specimens such that the specimens can later be restored to their isolated state with minimal damage.

These and other objects are accomplished by the method disclosed and will become apparent from the following detailed description of one preferred embodiment in conjunction with the accompanying drawings.

DETAILED DESCRIPTION

The present invention, generally described, provides compositions and methods for the preservation of biological samples. The compositions comprise *Acacia* Gum, including derivations and modifications thereof which are useful as a reversible preservation solution. *Acacia* Gum is a complex and highly branched carbohydrate polymer. The central core or nucleus is D-galactose and D-glucuronic acid, to which are attached sugars such as L-arabinose, L-rhamnose, and the like. *Acacia* Gum is available as thin flakes, powder, granules, or angular fragments which are completely soluble in hot and cold water.

*Acacia* Gum is a natural exudate or sap obtained from any of several plants belonging to the genus *Acacia*. *Acacia Senegal* and *Acacia Seyal* trees are the most commercially exploited species. *Acacia* Gum typically refers to the gum harvested from *Acacia Senegal* trees. *Acacia* plants are leguminous shrubs and trees that grow in warm regions, such as the Republic of the Sudan and the Upper Nile region of eastern Africa, where most of the world's *Acacia* Gum is harvested.

*Acacia* Gum was widely used in ancient Egypt in the preparation of inks and dyes and is thought to have been used as an adhesive for mummification bindings. An article of commerce for centuries, the name "Arabic Gum" is believed to have been derived from the fact that *Acacia* gum was typically shipped from Arabian ports to Europe. Today, *Acacia* Gum is used in the manufacture of printing inks, textile dyes, adhesives, pharmaceuticals, vitamins, confections, foods, beverages, cosmetics, and many other products. For example, *Acacia* Gum is used to make the water-soluble glue on postage stamps and envelopes, added to candies to prevent crystallization, used as a coating to flavor particles and beverages, added to beer to stabilize the foam, used as an emulsifier of fats in foods, lotions, and soaps, and is the most important gum in the manufacture of ink.

The botanical name for the *Acacia* Gum referred to in this application is *Acacia Nilotica* (*Linn.*), N. O. Leguminosae. *Acacia* Gum is water-soluble, edible, non-toxic, highly uniform, pale in color, and has excellent emulsifying and film-forming qualities. *Acacia* Gum consists mainly of high-molecular weight polysaccharides and their calcium, magnesium and potassium salts.

Figure 1:
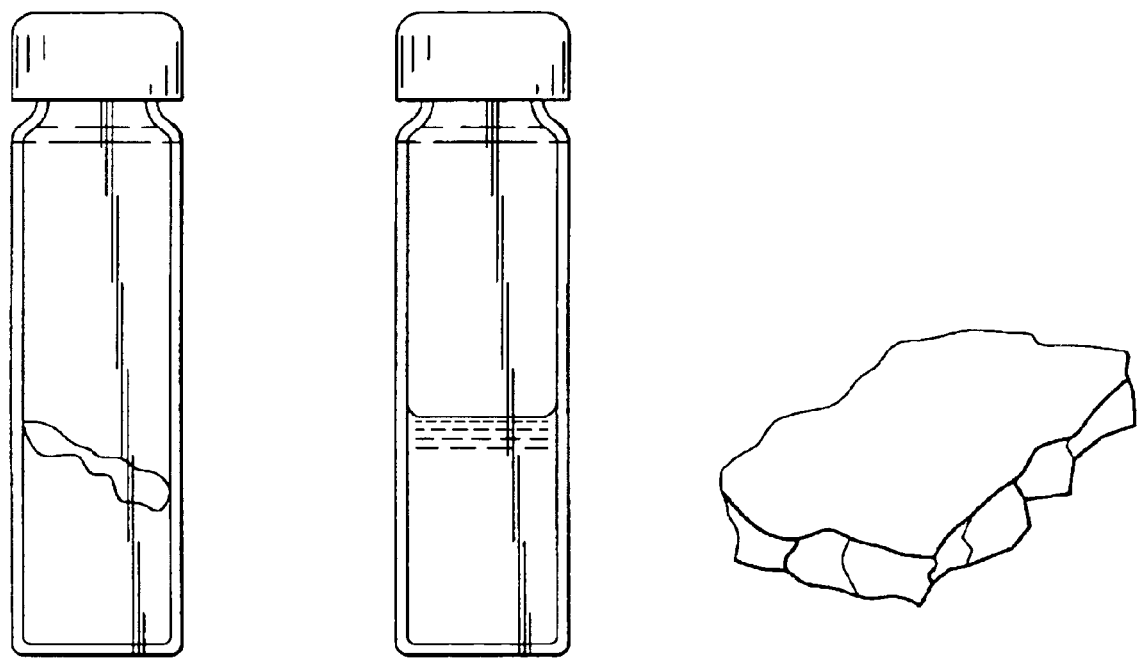
FIG. 1 is a photograph of *Acacia* Gum in powder form, liquid solution, and solid form.
Figure 2A:
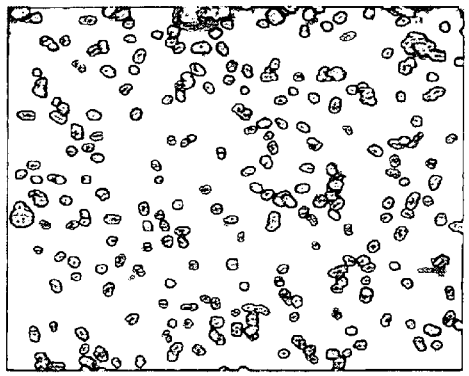
FIG. 2 is a series of photographs of bacteria at various stages of immobilization and restoration, according to an embodiment of the present invention.
Figure 2B:
Figure 2C:
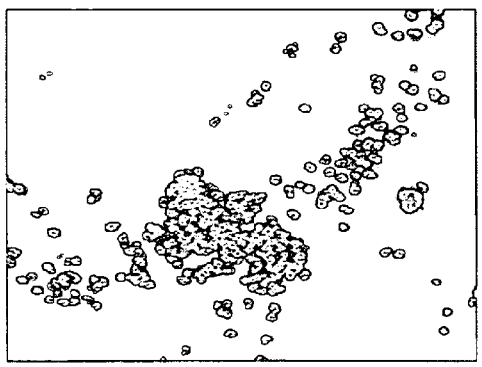
Figure 2D:
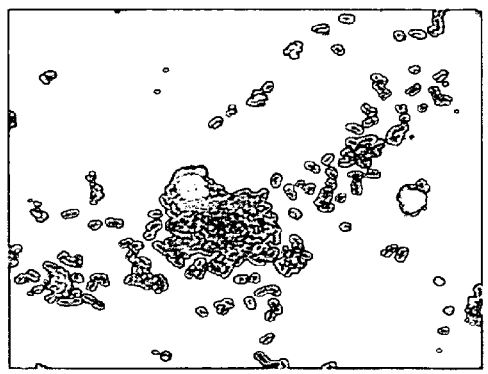
Figure 2E:
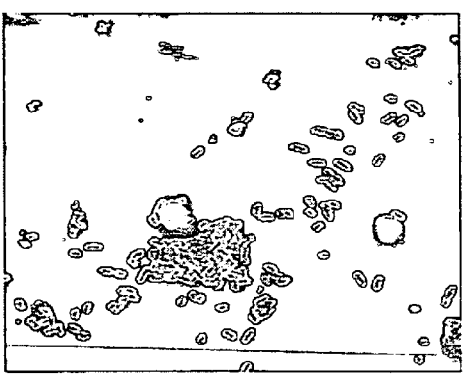
Figure 2F:
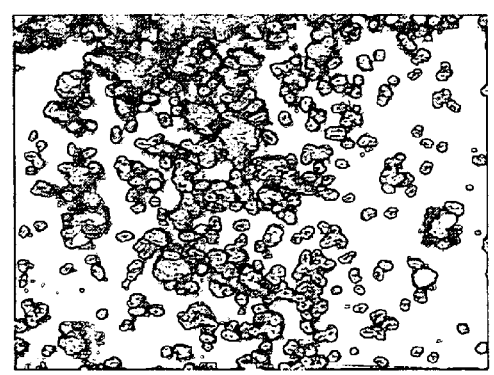
Figure 3:
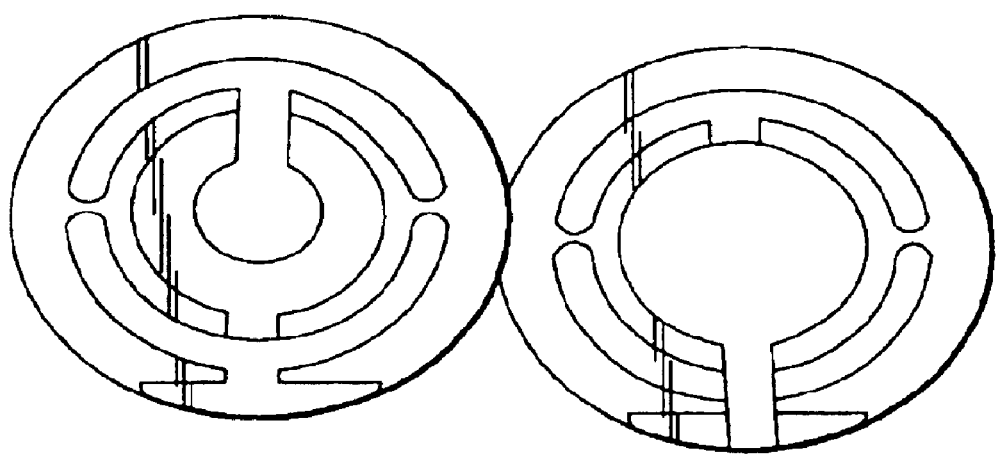
FIG. 3 is a photograph of crystal biosensors coated with a film of *Acacia* Gum solution, according to an embodiment of the present invention.

*Acacia* Gum is harvested by tapping the trunk of an *Acacia Senegal* tree, which causes the gum to seep out and solidify into colorless or pale yellow tear-shaped nodules. The dried nodules are typically gathered by hand. *Acacia* Gum is commercially available in the form of white or yellowish flakes, granules, or powder. *Acacia* Gum powder is plentiful and readily available commercially, at a low cost. When the powder form is dissolved in water, the resulting solution becomes increasingly viscous as the water evaporates, becoming a solid at room temperature. The photograph in FIG. 1 shows *Acacia* Gum powder in the vial on the left, *Acacia* Gum in aqueous solution in the other vial, and between the vials a solid sheet of *Acacia* Gum at room temperature.

The compositions of the invention are useful for the preservation of any biological sample of interest. Such samples include, without limitation, microorganisms, viruses, bacteria (such as as *E. coli, Salmonella, Listeria, Staphylococcus*, and others), phages, antibodies, antigens, DNA, RNA, receptors, enzymes, proteins, biochemicals, yeast and other fungi, and plant and animal cells and extracts. Animal cells and extracts include, without limitation, semen, sperm, ova, blood, tissue samples, cell samples, urine, saliva, lymphatic fluid, skin, hair, bones, and bone marrow. Additionally, biological samples include proteins, enzymes, antibodies, monoclonal antibodies and the like.

The phrase, "biological specimen in an isolated condition," as used herein indicates a biological sample that has been isolated and substantially purified; meaning that it is substantially or essentially free from components that normally accompany or interact with the sample as found in its natural environment.

Isolation and Preservation Technique

*Acacia* Gum powder is readily soluble in water. The solution becomes increasingly viscous as some of the water evaporates. An aqueous *Acacia* Gum solution is characterized by its reversibility. If more water is added, the viscosity decreases. Even if the solution is permitted to harden or cure into a solid, the addition of water will return the solid to an aqueous solution. Reversibility in this context also refers to the fact that the *Acacia* Gum solution can be separated nearly completely from the biological specimen after the preservation method of the present invention has been performed.

In one embodiment of the present invention, a biological specimen is preserved by being immersed in or otherwise combined with an effective amount of *Acacia* Gum or an *Acacia* Gum solution. The amount of *Acacia* Gum solution will vary depending upon sample size. The phrase "effective amount" is intended to indicate an amount sufficient to form a suspension; that is, to suspend the biological molecules or units of the specimen within the *Acacia* Gum solution.

Initially upon being immersed in the solution, biological material such as bacteria remain active and motile. As the viscosity increases, activity and motility decrease. In one embodiment, the suspension may be stirred to ensure a good distribution of specimen or to speed the evaporation of water and thus accelerate the curing process. Curing may take place in ambient conditions; in other words, at room temperature and at normal atmospheric pressures. When the solution solidifies, the bacteria shrink to about one-half to one-third of their original size. While the invention is not bound by any particular mechanism of action, it is postulated that the *Acacia* Gum solution penetrates the cell membrane of the biological material, possibly replacing the water and resulting in the overall shrinkage observed. Inside the resulting solid, the bacteria remain dormant and may be kept at room temperature.

In one embodiment, the solid material containing the biological specimen may be made into a powder, pellets, tablets, flakes, plates, capsules, or other forms or containers. The solid is transparent to visible light, a feature that makes it suitable for viewing and for certain optical applications. Moreover, although the solid is water-soluble, the solid is resistant to almost all organic solvents and most acids.

To restore the biological material to its isolated condition, the solid is irrigated with an aqueous solution. The amount of aqueous solution needed to change the solid back into a suspension will vary depending upon the sample size. The phrase “effective amount of aqueous solution” is intended to indicate an amount sufficient to transform the solid into a suspension.

In one aspect of the invention, the aqueous solution used to irrigate the solid contains distilled water, a buffer, and one or more salt compounds such as potassium chloride, sodium chloride, magnesium chloride, and calcium chloride. The buffer is a substance capable in solution of neutralizing both acids and bases and, thereby, maintaining the original pH of the solution. One such pH buffer in common use is 3-(N-morpholino) propanesulfonic acid (also known as MOPS). Another common pH buffer is called a phosphate buffer. A phosphate buffer, in one form, contains anhydrous monosodium phosphate and trisodium phosphate dodecahydrate. A phosphate buffer solution may contain different molar ratios of monosodium phosphate and trisodium phosphate, depending upon the value of the pH to be maintained.

When irrigated, the solid gradually dissolves and the biological specimen is again suspended within an *Acacia* Gum solution. The viscosity of the suspension decreases as more aqueous solution is added. The biological specimen returns to its normal size, absorbing the water lost or exchanged during the curing process.

In another aspect of the present invention, the suspension of biological material and *Acacia* Gum solution is reversible because it can be separated. The *Acacia* Gum solution can be removed using common methods of separating mixtures, leaving the biological specimen in its isolated condition. The separation step restores the biological specimen to its former isolated or prepared condition. The phrase “substantially restored” is intended to describe the nearly complete separation of the *Acacia* Gum solution from the biological specimen and the nearly complete restoration of viability of the biological specimen.

Biosensors

The methods of the invention find particular use in preserving biological samples on biosensors. A biosensor, as shown in FIG. 3, is comprised of a biological receptor, an interface, and a signal transducer. The biochemical signal produced when a sample is placed on the biological receptor is converted or translated by the signal transducer into a quantifiable electrical signal.

The biological receptor is selected to sense a specific target compound called the analyte. For example, a copper receptor will absorb copper molecules from a sample. The signal transducer converts the activity on the receptor (e.g., the accumulation of copper molecules) into an electrical signal. For example, the signal transducer can detect the increased mass of the biosensor by sensing changes in certain electrical properties.

The types of biological receptors in use include, without limitation, enzymes, antibodies, phages, and lipid layers. The biological receptor must be prepared such that it will respond to the analyte. Preparation of the biological receptor includes depositing the biological material onto the interface. Preparation of the interface to receive the biological receptor may include chemical etching of the interface, the application of thin membranes, coating the interface with a thin layer of a particular biochemical to serve as an anchor for the biological receptor, or any other of a variety of preparation methods. The phrase, “biological specimen in a prepared condition,” as used herein indicates a biological receptor that has been isolated and deposited upon the biosensor interface using any preparation technique that renders the receptor ready for its intended use.

The signal transducer is typically an electrode connected to the interface to measure any change in the receptor when the sample is introduced. Signal transducer systems include, without limitation, piezoelectric crystals, conductimeters, enzyme-sensing electrodes, thermistors, optoelectronic and fiber-optic devices, field-effect transistors, gas-sensing electrodes, and ion-selective electrodes. The signal transducer itself may be a pH-electrode, an oxygen electrode, or a piezoelectric crystal.

In a common biosensor using quartz crystal technology, shown in FIG. 3, the biological receptor is deposited in a film onto a piezoelectric crystal, which serves as the interface. An electrode attached to the crystal acts as the signal transducer. The quartz crystal is oscillated at a known frequency based on its total mass, including the mass of the film receptor. When a sample containing the analyte is placed on the receptor, the total mass will change when the antibodies in the receptor bind to the analyte. In response to the change in mass, the frequency of the crystal oscillation will change, and the change in frequency is measured by the signal transducer. Because frequency and mass are related, the additional mass can be calculated, indicating the precise amount of the analyte present in the sample.

The Biosensor Experiment

A biosensor with a biological receptor comprised of antibodies against *Salmonella* bacteria was covered with a film of *Acacia* Gum solution. After curing and storage at room temperature for a period of four (4) days, the antibodies were released by irrigation with water containing 55.0 milli-Molar potassium chloride, 4.0 milli-Molar sodium chloride, 1.0 milli-Molar magnesium chloride, 0.1 milli-Molar calcium chloride, and 2.0 milli-Molar 3 -(N-morpholino) propanesulfonic acid, used as a pH buffer. Preliminary data was obtained demonstrating the sensitivity of the restored sensors compared to the uncoated sensors, as shown in FIG. 4 and Table One.

Table One.Performance of Coated *Salmonella* Biosensors.

TABLE ONE

Performance of Coated Salmonella Biosensors.

|  | Uncoated | Coated (Group 1) | Coated (Group 2) |
|---|---|---|---|
| Total Sensors | 9 | 4 | 22 |
| Good Sensors | 4 | 1 | 8 |
| Yield (%) | 44.4% | 25.0% | 36.4% |
| Slope (mV per decade) | 15.3 | 7.6 | 19.4 |

Measurements were carried out with a Quartz Crystal Microbalance (QCM) measurement system. More specifically, the biosensors used in this experiment were the PM-700 series quartz sensor crystals available from Maxtek, Inc. The output of the sensor crystal corresponds to the change in total mass. The signal transducer measures the change in the crystal in millivolts (mV). Referring to Table One and the graphs shown in FIG. 4, the "mV per decade" refers to the voltage change for each order of magnitude change in the bacterial concentration.

The bacterial suspension of approximately $10^9$ cells per milliliter was diluted 10, 100, and 1000 times, respectively. The relative concentrations of bacteria were, therefore, 1, $10^{-1}$, $10^{-2}$, and $10^{-3}$. Accordingly, the logarithms (shown in FIG. 4) of the relative concentrations were 0, −1, −2, and −3, respectively.

For purposes of this experiment, a "good sensor" has a sensitivity of more than 7.0 mV per decade. The observation that only 44.4 percent of the uncoated biosensors were "good sensors" indicates the inherent fragility of the biological receptors used in biosensors.

Figure 4:
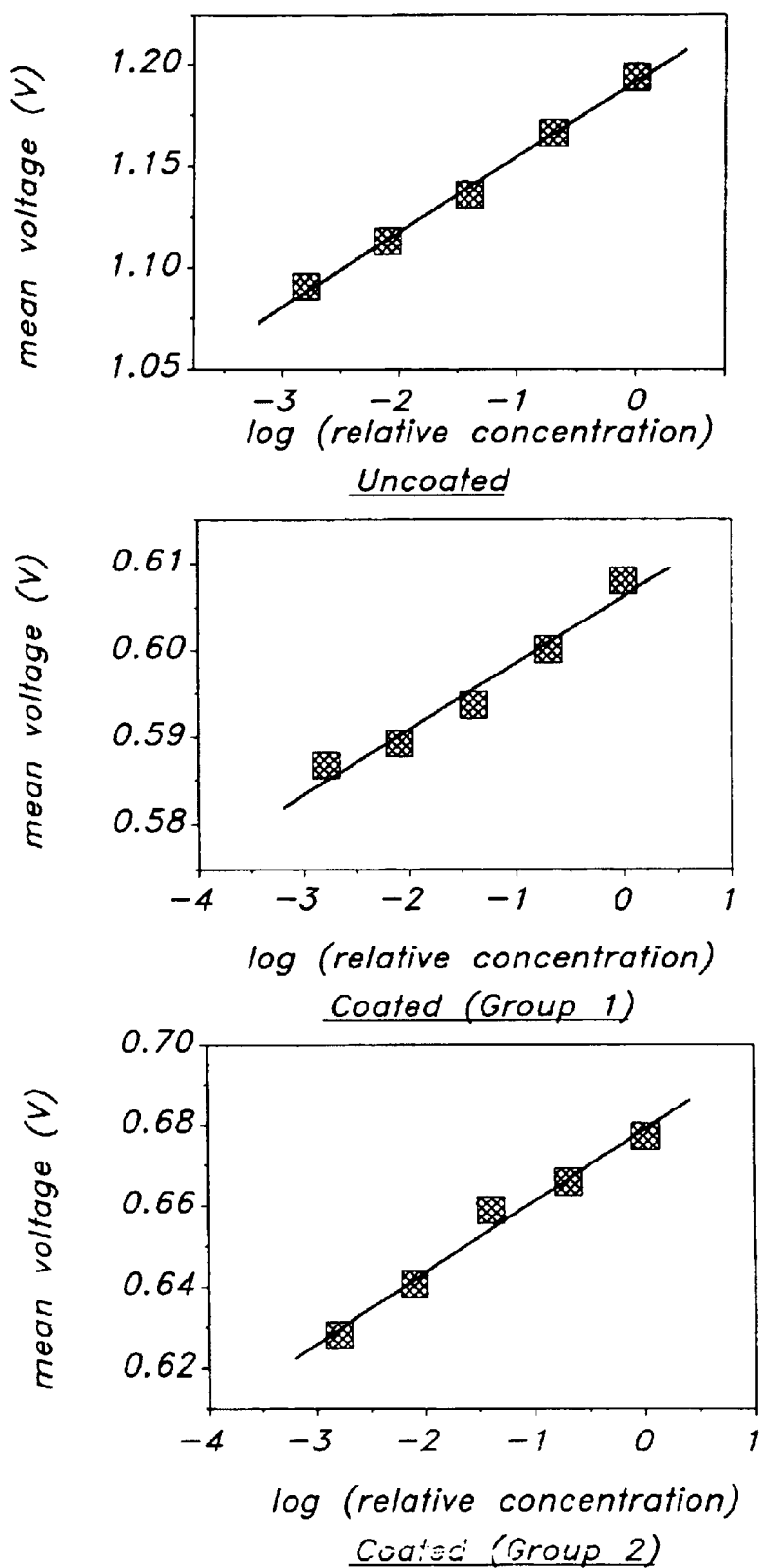
FIG. 4 is a series of graphs representing the results of experimentation conducted according to an embodiment of the present invention.

The slope of the graphs shown in FIG. 4 indicates the degree of sensitivity of the biosensor. The uncoated biosensors had a sensitivity of 15.3 mV per decade. While the sensitivity of Group 1 decreased to 7.6 mV, the sensitivity of the coated biosensors in Group 2 was observed to be 19.4 mV—better than the sensitivity of the uncoated sensors. In both cases, the biosensors which had been coated with the *Acacia* Gum solution were fully operational and ready to use.

The Bull Sperm Experiment

In another aspect, the methods of the invention are useful in preserving animal cells and extracts, such as sperm. In another experiment, the isolation and preservation technique of the present invention was used to temporarily and reversible preserve bull sperm.

A sample of bull sperm was immobilized in *Acacia* Gum solution, where it remained at room temperature for a period of four (4) days before being released by irrigation with water. Although reproduction was not tested, the bull sperm showed no difference in motility when compared to the initial sample.

The present invention may be used to preserve bull sperm for transport or storage, at room temperature, without significant damage to the sperm. The cryogenic preparation and storage of bull sperm is expensive and destructive because of crystalline structures formed during freezing. In contrast, the present invention does not introduce crystals or other destructive structures into the sample and it is much less expensive.

Bacterial Cultures

The methods of the present invention are also useful in preserving samples of bacteria. Two separate experiments were conducted to test the response and subsequent viability of bacteria suspended within an *Acacia* Gum solution.

In a first experiment, separate samples of *Escherichia coli* O157 (*E. coli*) bacteria and *Salmonella* bacteria were immobilized in *Acacia* Gum solution, where each sample remained at room temperature for a period of seven (7) days. The bacteria were released by irrigation with water containing a phosphate buffer (pH 7.4) containing 2.7 milli-Molar potassium chloride and 137 milli-Molar sodium chloride. The released bacteria showed no difference in motility when compared to the initial culture. The bacteria reproduced normally.

FIG. 2 shows the *Salmonella* bacteria at different stages of the experiment. Slide a shows the bacteria immersed in the *Acacia* Gum solution. Slide b shows the bacteria immobilized within the *Acacia* Gum solution, which has become a solid at room temperature. Notice that the bacteria in Slide b are somewhat smaller.

After remaining immobilized for seven (7) days, the bacteria were irrigated with an aqueous solution. The restoration process is shown in Slides c, d, e, and f. Slide c shows the condition of the bacteria after one minute. Some motion was observed after two minutes, shown in Slide d. Slide e shows the condition of the bacteria after three minutes. After ten minutes, as shown in Slide f, the bacteria have returned to their normal size, absorbing the water lost during the immobilization or curing process.

In a second experiment, two additional samples of *E. coli* and *Salmonella* bacteria were immobilized in *Acacia* Gum solution for a period of twenty-one (21) days, with the same results. The bacteria showed no difference in motility when compared to the initial culture and the bacteria reproduced normally.

Other Uses

The present invention offers a method of reversibly preserving biological specimens in a variety of contexts. The isolation and preservation techniques of the present invention could be used, without limitation, for isolating microbial cultures for shipment, blood isolation and storage, time-release capsules for pharmaceuticals, biodegradable packaging, soluble prostheses and implants, surgery, and forensics.

The *Acacia* Gum solution and the isolation and preservation techniques of the present invention represent a simple, rapid, and inexpensive alternative to many of the biological preservation techniques in use today. *Acacia* Gum is organic, water-soluble, bio-compatible, biodegradable, and non-toxic. The preservation of biological specimens with *Acacia* Gum is reversible and causes little or no damage to the specimen.

While this invention has been described in specific detail with reference to the disclosed embodiments, it will be understood that many variations and modifications may be effected without departing from the invention as described in the appended claims.

What is claimed is:

1. A method of reversibly preserving a microorganism, comprising:
  combining said microorganism in an isolated condition with an effective amount of an *Acacia* Gum solution to form a suspension; and
  curing said suspension in ambient conditions to form a solid containing said microorganism in a dormant and preserved state.

2. The method of claim 1, wherein said *Acacia* Gum solution comprises a quantity of solid *Acacia* Gum dissolved in a quantity of distilled water.

3. The method of claim 1, wherein said step of curing further comprises stirring said suspension.

4. The method of claim 1, wherein said step of combining comprises immersing said microorganism into an effective amount of an *Acacia* Gum solution.

5. The method of claim 1, wherein said step of curing further comprises distributing said suspension over a surface to accelerate curing.

6. A method of restoring a reversibly preserved microorganism, said microorganism in an isolated condition having been combined with an effective amount of an *Acacia* Gum solution to form a suspension, said suspension having been cured to form a solid containing said microorganism in a dormant and preserved state, said method comprising:

irrigating said solid in ambient conditions with an effective amount of an aqueous solution to restore said suspension; and separating said suspension such that said microorganism is substantially restored to said isolated condition.

7. The method of claim 6, wherein said aqueous solution comprises a quantity of distilled water, a buffer, and a quantity of one or more compounds selected from the group consisting of potassium chloride, sodium chloride, magnesium chloride, and calcium chloride.

8. The method of claim 6, wherein said buffer comprises a quantity of 3-(N-morpholino) propanesulfonic acid.

9. A method of reversibly preserving semen, comprising:

combining said semen in an isolated condition with an effective amount of an *Acacia* Gum solution to form a suspension; and curing said suspension in ambient conditions to form a solid containing said semen in a dormant and preserved state.

10. The method of claim 9, wherein said *Acacia* Gum solution comprises a quantity of solid *Acacia* Gum dissolved in a quantity of distilled water.

11. The method of claim 9, wherein said step of curing further comprises stirring said suspension.

12. The method of claim 9, wherein said step of combining comprises immersing said semen into an effective amount of an *Acacia* Gum solution.

13. The method of claim 9, wherein said step of curing further comprises distributing said suspension over a surface to accelerate curing.

14. A method of restoring reversibly-preserved semen, said semen in an isolated condition having been combined with an effective amount of an *Acacia* Gum solution to form a suspension, said suspension having been cured to form a solid containing said semen in a dormant and preserved state, said method comprising:

irrigating said solid in ambient conditions with an effective amount of an aqueous solution to restore said suspension; and separating said suspension such that said semen is substantially restored to said isolated condition.

15. The method of claim 14, wherein said aqueous solution comprises a quantity of distilled water, a buffer, and a quantity of one or more compounds selected from the group consisting of potassium chloride, sodium chloride, magnesium chloride, and calcium chloride.

16. The method of claim 14, wherein said buffer comprises a quantity of 3-(N-morpholino) propanesulfonic acid.

* * * * *